United States Patent
Hamaguchi

(10) Patent No.: US 12,362,045 B2
(45) Date of Patent: *Jul. 15, 2025

(54) INFORMATION PROCESSING APPARATUS, INFORMATION PROCESSING METHOD, AND PROGRAM

(71) Applicant: FUJIFILM Corporation, Tokyo (JP)

(72) Inventor: Yuya Hamaguchi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 492 days.

This patent is subject to a terminal disclaimer.

(21) Appl. No.: 17/844,033

(22) Filed: Jun. 19, 2022

(65) Prior Publication Data
US 2022/0327158 A1    Oct. 13, 2022

Related U.S. Application Data

(63) Continuation of application No. PCT/JP2020/040861, filed on Oct. 30, 2020.

(30) Foreign Application Priority Data

Dec. 26, 2019 (JP) .................. 2019-236342

(51) Int. Cl.
    *G16C 20/40* (2019.01)
    *G06F 16/583* (2019.01)
    (Continued)

(52) U.S. Cl.
    CPC ........... *G16C 20/40* (2019.02); *G06F 16/583* (2019.01); *G06T 7/00* (2013.01); *G06V 30/194* (2022.01); *G06V 40/161* (2022.01)

(58) Field of Classification Search
    None
    See application file for complete search history.

(56) References Cited

U.S. PATENT DOCUMENTS

| | | | |
|---|---|---|---|
| 5,751,850 A | * | 5/1998 | Rindtorff ............. G06V 30/155 382/179 |
| 10,372,713 B1 | * | 8/2019 | Blake .................... G16C 20/70 |

(Continued)

FOREIGN PATENT DOCUMENTS

| | | |
|---|---|---|
| CN | 102436447 | 5/2012 |
| CN | 108062529 | 5/2018 |

(Continued)

OTHER PUBLICATIONS

Staker et al., "Molecular Structure Extraction from Documents Using Deep Learning," arXiv:1802.04903, https://doi.org/10.48550/ arXiv.1802.04903, Feb. 14, 2018 (Year: 2018).*

(Continued)

*Primary Examiner* — Soo Shin
(74) *Attorney, Agent, or Firm* — JCIPRNET

(57) ABSTRACT

There are provided an information processing apparatus, an information processing method, and a program with which structural elements in a structural formula can be identified from an image showing the structural formula and the results of identification can be used in a compound search performed later on.

An information processing apparatus includes a processor, and the processor is configured to identify, on the basis of feature values of respective regions in a subject image showing a structural formula of each subject compound among subject compounds, structural elements shown by the respective regions among structural elements in the structural formula of the subject compound, by using an identification model, and store element information about the identified structural elements in the structural formula of each subject compound in association with the subject compound The identification model is a model created (Continued)

through machine learning using a learning image showing one structural element in a structural formula of a compound.

20 Claims, 8 Drawing Sheets

(51) Int. Cl.
  *G06T 7/00* (2017.01)
  *G06V 30/194* (2022.01)
  *G06V 40/16* (2022.01)

(56) References Cited

U.S. PATENT DOCUMENTS

| | | | | |
|---|---|---|---|---|
| 2012/0084299 | A1* | 4/2012 | Cai | G16C 20/40 |
| | | | | 707/E17.084 |
| 2019/0251455 | A1* | 8/2019 | Spangler | G06N 20/00 |
| 2019/0286669 | A1 | 9/2019 | Li et al. | |
| 2020/0349451 | A1* | 11/2020 | Suzuki | G06N 3/045 |
| 2022/0309815 | A1* | 9/2022 | Hamaguchi | G06V 30/18057 |

FOREIGN PATENT DOCUMENTS

| | | |
|---|---|---|
| CN | 108334839 | 7/2018 |
| CN | 110265091 | 9/2019 |
| JP | H04114560 | 4/1992 |
| JP | H0728940 | 1/1995 |
| JP | 2013061886 | 4/2013 |
| JP | 2014091724 | 5/2014 |
| JP | 2014182663 | 9/2014 |
| WO | 2019048965 | 3/2019 |
| WO | 2019175271 | 9/2019 |

OTHER PUBLICATIONS

Keyrouz et al., "Chemical Structure Recognition and Prediction: A Machine Learning Technique," 2018 IEEE Conference on Computational Intelligence in Bioinformatics and Computational Biology (CIBCB) (Year: 2018).*
Greg Landrum, "RDKit Documentation Release 2012.12.1," Jan. 22, 2013 (Year: 2013).*
Tang et al., "A Progressive Structural Analysis Approach for Handwritten Chemical Formula Recognition," 2013 12th International Conference on Document Analysis and Recognition (Year: 2013).*
Zheng et al., "Recognition of Handwritten Chemical Organic Ring Structure Symbols Using Convolutional Neural Networks," 2019 International Conference on Document Analysis and Recognition Workshops (ICDARW) (Year: 2019).*
Joshua Staker et al., "Molecular Structure Extraction From Documents Using Deep Learning", Journal of Chemical Information and Modeling, Mar. 2019 , pp. 1-16.
"Office Action of China Counterpart Application", issued on Sep. 3, 2024, with English translation thereof, pp. 1-13.
Office Action of Japan Counterpart Application, with English translation thereof, issued on Nov. 14, 2023, pp. 1-6.
"Office Action of Japan Counterpart Application" with English translation thereof, issued on Jul. 4, 2023, p. 1-p. 6.
Nishiha, "Estimating Molecular Formulae from Structural Formula Images in Rdkit", Jan. 2019, submit with English description extracted from ISA237, https://qiita.com/nishiha/items/f20f9942a1c35e1ea1fd.
Hideo Ito, "Image Searching in Patent Information Services", Japan Patent Office Technology Forum, submit with partial English translation, pp. 66-70.
"International Search Report (Form PCT/ISA/210) of PCT/JP2020/040861," mailed on Feb. 2, 2021, with English translation thereof, pp. 1-5.
"Written Opinion of the International Searching Authority (Form PCT/ISA/237) of PCT/JP2020/040861," mailed on Feb. 2, 2021, with English translation thereof, pp. 1-8.

* cited by examiner

SUBJECT COMPOUND INFORMATION

| SUBJECT COMPOUND | PUBLICATION NO. | PAGE | x COORDINATE OF COMPOUND | y COORDINATE OF COMPOUND | x WIDTH OF COMPOUND | y HEIGHT OF COMPOUND |
|---|---|---|---|---|---|---|
| A | PATENT PUBLICATION NO. 2000-000001 | 4 | 50 | 50 | 50 | 50 |
| B | PATENT PUBLICATION NO. 2004-000333 | 8 | 20 | 20 | 20 | 20 |
| C | PATENT NO. 5555555 | 21 | 35 | 35 | 35 | 35 |

FIG. 2B

ELEMENT INFORMATION

| TYPE OF STRUCTURAL ELEMENT | ACCURACY | x COORDINATE OF STRUCTURAL ELEMENT | y COORDINATE OF STRUCTURAL ELEMENT | x WIDTH OF STRUCTURAL ELEMENT | y WIDTH OF STRUCTURAL ELEMENT |
|---|---|---|---|---|---|
| Double | 1 | 3 | 258 | 32 | 76 |
| BendC | 0.98 | 10 | 310 | 28 | 30 |
| BendC | 0.92 | 10 | 252 | 25 | 28 |
| BendC | 0.99 | 54 | 229 | 26 | 30 |
| BendC | 0.75 | 55 | 327 | 27 | 38 |
| Double | 1 | 60 | 314 | 61 | 42 |
| Double | 1 | 62 | 227 | 59 | 50 |
| BendC | 0.98 | 102 | 309 | 27 | 31 |
| BendC | 0.98 | 102 | 251 | 26 | 30 |
| O | 0.95 | 150 | 45 | 36 | 37 |
| BendC | 0.99 | 154 | 225 | 28 | 34 |
| BendC | 0.78 | 157 | 333 | 23 | 30 |
| BendC | 0.9 | 160 | 168 | 17 | 22 |
| Double | 0.99 | 161 | 231 | 60 | 46 |
| Double | 1 | 162 | 314 | 59 | 42 |
| Double | 0.88 | 178 | 57 | 47 | 45 |
| O | 0.97 | 199 | 133 | 37 | 37 |
| BendC | 0.98 | 203 | 307 | 26 | 32 |
| BendC | 0.99 | 204 | 252 | 26 | 30 |
| BendC | 0.95 | 206 | 75 | 24 | 32 |
| BendC | 0.99 | 254 | 47 | 28 | 34 |
| BendC | 0.98 | 255 | 229 | 26 | 30 |
| BendC | 0.5 | 259 | 333 | 23 | 31 |
| Double | 0.97 | 261 | 56 | 63 | 47 |
| Double | 1 | 262 | 313 | 62 | 44 |
| Double | 1 | 263 | 231 | 58 | 49 |
| BendC | 0.97 | 301 | 255 | 27 | 27 |
| BendC | 1 | 302 | 307 | 24 | 29 |

FROM FIG. 2A

FIG. 7

[Chem. 33]

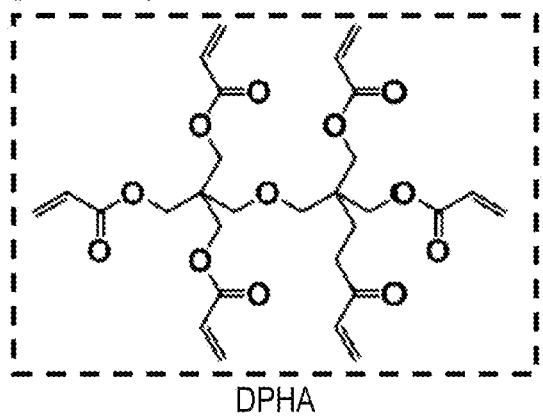

DPHA

[0143]

[Examples 13 and 14]

A method the same as that in Example 12 was used except for the transparent resin layer forming composite A being changed to transparent resin layer forming composites B and C shown below in formation of the transparent resin layer, and laminates according to Examples 13 and 14 were obtained.

[0144]

Transparent resin layer forming composite B

| | |
|---|---:|
| • CEL2021P shown below (from Daicel) | 144 parts by mass |
| • IRGACURE127 shown below (from BASF) | 3 parts by mass |
| • CPI-100P shown below (propylene carbonate solution) | 6 parts by mass |
| • Megaface RS-90 (from DIC) | 0.3 parts by mass |
| • Methyl ethyl ketone (MEK) | 347 parts by mass |

[0145]

CEL2021P

[Chem. 34]

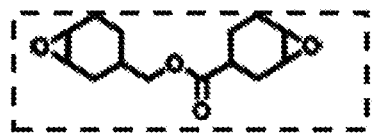

[0146]

IRGACURE127

[Chem. 35]

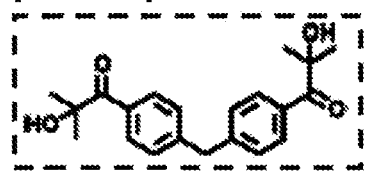

[0147]

Photocationic polymerization initiator (CPI-100P)

FIG. 8

```
Search Results

Compound A (Patent Application No. ****-******, page x)  Degree of similarity: 95%

Compound B (Patent Application No. ****-******, page x)  Degree of similarity: 87%

Compound C (Patent Application No. ****-******, page x)  Degree of similarity: 80%

Compound D (Patent Application No. ****-******, page x)  Degree of similarity: 73%

Compound E (Patent Application No. ****-******, page x)  Degree of similarity: 50%
```

FIG. 9
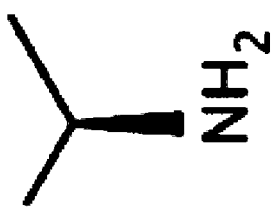
$\Phi(C) = (0, 0, 0, 0, 1, 0, 0, \ldots\ldots)$

INFORMATION PROCESSING APPARATUS, INFORMATION PROCESSING METHOD, AND PROGRAM

CROSS-REFERENCE TO RELATED APPLICATIONS

This application is a Continuation of PCT International Application No. PCT/JP2020/040861 filed on Oct. 30, 2020, which claims priority under 35 U.S.C. § 119(a) to Japanese Patent Application No. 2019-236342 filed on Dec. 26, 2019. The above application is hereby expressly incorporated by reference, in its entirety, into the present application.

BACKGROUND OF THE INVENTION

1. Field of the Invention

The present invention relates to an information processing apparatus, an information processing method, and a program and specifically relates to an information processing apparatus, an information processing method, and a program that enable a search for a structural formula of a compound shown as an image.

2. Description of the Related Art

It is often the case that a structural formula of a compound is managed as image data and, for example, such image data is posted on the Internet or is incorporated into document data. However, with a usual search method, it is difficult to search for a structural formula of a compound managed as image data.

To enable a search for a structural formula of a compound shown by an image, a technique has been developed in which an automatic recognition technique using a computer is used to recognize a structural formula of a compound from an image of the structural formula. Specific examples of the technique include techniques described in JP2013-61886A and JP2014-182663A.

In the technique described in JP2013-61886A, text information in a chemical structure drawing (for example, atoms that constitute a compound) is recognized by pattern recognition, and line diagram information of the chemical structure drawing (for example, a bond between atoms) is recognized by using a predetermined algorithm.

In the technique described in JP2014-182663A, an image of a structural formula of a compound is read, a pixel representing an atomic symbol in the image is assigned a value indicating an attribute of the atomic symbol, and a pixel representing a bond symbol in the image is assigned a value indicating an attribute of the bond symbol.

SUMMARY OF THE INVENTION

In the techniques described in JP2013-61886A and JP2014-182663A, a rule is established on correspondences between regions in an image that shows a structural formula of a compound and structural elements, in the structural formula, shown by the respective regions. Then, the structural elements in the structural formula shown by the image are identified in accordance with the rule.

However, as the depicting format for a structural formula, a plurality of equivalent formats are available, and a thickness, an orientation, and so on in the structural formula may change depending on the way of drawing. In this case, to cope with different ways of drawing of the structural formula, a large number of rules for identifying structural elements in the structural formula depicted in various ways of drawing need to be established in advance. For a structural formula depicted in a way of drawing for which an identification rule is not established, it is difficult to identify structural elements included in the structural formula.

Meanwhile, when structural elements in a structural formula of a certain compound are identified from an image showing the structural formula, information about the identified structural elements can be used as information useful in a search for the compound performed later on.

The present invention has been made in view of the above-described circumstances and addresses the above-described issues in the related art. Specifically, an object of the present invention is to provide an information processing apparatus, an information processing method, and a program with which structural elements in a structural formula can be identified from an image showing the structural formula regardless of the way of drawing of the structural formula and the results of identification can be used in a compound search performed later on.

To achieve the above-described object, an information processing apparatus of the present invention is an information processing apparatus including a processor, the processor being configured to identify, on the basis of feature values of respective regions in a subject image showing a structural formula of each subject compound among subject compounds, structural elements shown by the respective regions among structural elements in the structural formula of the subject compound, by using an identification model, and store element information about the identified structural elements in the structural formula of each subject compound in association with the subject compound, the identification model being created through machine learning using a learning image showing one structural element in a structural formula of a compound.

When a plurality of learning images each of which is the learning image and which show the structural element having the same chemical structure and in different depicting formats are used in the machine learning, the identification model that derives a common feature value from the plurality of learning images may be created through the machine learning.

Preferably, the processor is configured to obtain input information about a search compound, and search for a subject compound corresponding to the search compound, among the subject compounds for each of which the element information is stored, on the basis of the input information and the element information associated with each subject compound.

In the above-described configuration, more preferably, the processor is configured to calculate a degree of similarity between the search compound and each subject compound on the basis of the input information and the element information stored in association with the subject compound, and retrieve, as the search compound, a subject compound for which the degree of similarity satisfies a search condition, from among the subject compounds for each of which the element information is stored.

Further, more preferably, the processor is configured to obtain the input information that is information about a structural element included in a structural formula of the search compound.

The processor may be configured to detect the subject image from a document that includes the subject image, and identify the structural elements shown by the respective regions in the subject image by inputting the detected subject image in the identification model.

In the above-described configuration, more preferably, the processor is configured to detect the subject image from the document by using an object detection algorithm.

The element information may include information indicating a type of each structural element among the identified structural elements in the structural formula of the subject compound. In this case, the element information may further include information indicating a location of each structural element among the identified structural elements in the structural formula of the subject compound, in a coordinate space set for the subject image.

In the above-described configuration, the information indicating the type of each structural element among the structural elements may be information indicating a type of an atom or a bond between atoms corresponding to the structural element.

Alternatively, the information indicating the type of each structural element among the structural elements may be information indicating a chemical formula of a functional group corresponding to the structural element.

Alternatively, the information indicating the type of each structural element among the structural elements may be information formed of a part of a molecular fingerprint indicating, for each type of structural element, presence or absence of the structural element in the structural formula of the subject compound.

The above-described object can be achieved as an information processing method in which a processor is configured to perform a step of identifying, on the basis of feature values of respective regions in a subject image showing a structural formula of each subject compound among subject compounds, structural elements shown by the respective regions among structural elements included in the structural formula of the subject compound, by using an identification model, and a step of storing element information about the identified structural elements in the structural formula of each subject compound in association with the subject compound, the identification model being created through machine learning using a learning image showing one structural element in a structural formula of a compound.

Further, a program for causing a processor to perform steps in the information processing method described above can be implemented.

According to the present invention, structural elements in a structural formula can be identified from an image showing the structural formula regardless of the way of drawing of the structural formula and the results of identification can be used in a compound search performed later on.

BRIEF DESCRIPTION OF THE DRAWINGS

FIGS. 2A and 2B are diagrams illustrating an example database in which element information is stored for each compound;

FIG. 7 is a diagram illustrating a state where a plurality of subject images are detected from one document;

FIG. 8 is a diagram illustrating an example screen on which search results of subject compounds are displayed; and FIG. 9 is a diagram for explaining a molecular fingerprint.

DESCRIPTION OF THE PREFERRED EMBODIMENTS

An information processing apparatus, an information processing method, and a program according to one embodiment of the present invention (hereinafter referred to as "present embodiment") will be described below with reference to the attached drawings.

Note that the embodiment described below is only an example provided in order to explain the present invention in an easy-to-understand manner and is not intended to limit the present invention. That is, the present invention is not limited to the embodiment described below and can be modified or changed in various manners without departing from the spirit of the present invention. As a matter of course, the present invention includes its equivalents.

Further, in the following description, unless otherwise noted, "document" and "image" are an electronic document and an electronic image (in the form of data) respectively, each of which is information (data) that can be processed by a computer.

Functions of Information Processing Apparatus of the Present Embodiment

The information processing apparatus of the present embodiment (hereinafter simply referred to as "information processing apparatus") includes a processor and is capable of analyzing an image (subject image) that shows a structural formula of a subject compound and identifying structural elements in the structural formula. A subject compound is, for example, a compound for which its structural formula is shown by an image in a document and structural elements shown by respective regions in the image are identified by the information processing apparatus.

An image that shows a structural formula is an image of a line diagram that shows the structural formula. A plurality of equivalent depiction methods are available as the depiction method for a structural formula. Examples of the depiction methods include a method in which a single-bond hydrogen atom (H) is omitted, a method in which a skeletal carbon atom (C) is omitted, and a method in which a functional group is indicated by its abbreviation. The line diagram may change in accordance with the way of drawing (for example, the thickness and length of a bond line between atoms and the orientation in which a bond line extends). In the present embodiment, the way of drawing of a structural formula includes the resolution of an image that shows the structural formula.

Each structural element in a structural formula indicates an atom that constitutes the structural formula, a bond line between atoms, or a combination thereof. In the present embodiment, as illustrated in FIG. 1, individual atoms (for example, "Bend C" and "O" in FIG. 1) that constitute the structural formula and each individual bond line (for example, "Double" in FIG. 1) are structural elements.

Figure 1:
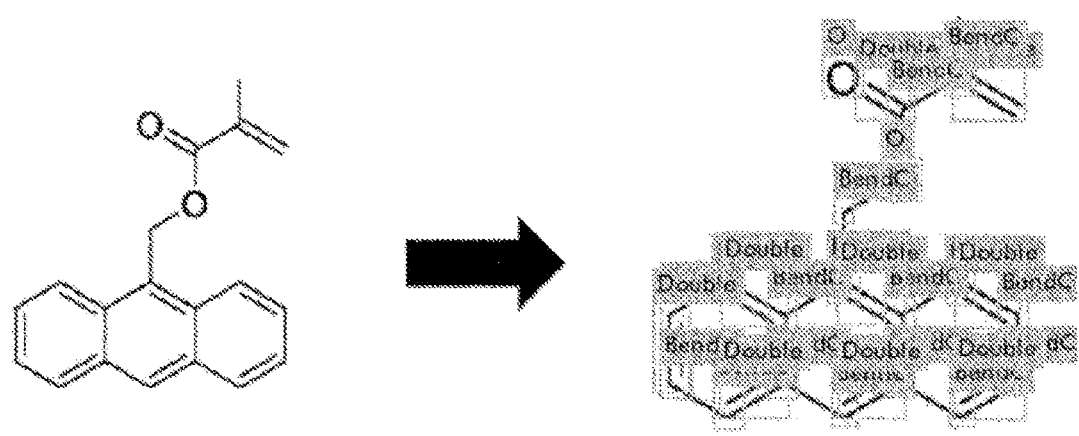
FIG. 1 is a diagram for explaining structural elements in a structural formula of a compound.

Each region in an image that shows a structural formula is a part that shows a structural element in the structural formula, and is, for example, a rectangular region in which the structural element is enclosed (see the right-hand figure in FIG. 1). The present embodiment assumes that one structural element is included per region. That is, in an image that shows a structural formula, a number of regions corresponding to structural elements included in the structural formula are present.

The information processing apparatus performs machine learning by using as a learning data set, one structural element in a structural formula of a compound (more specifically, label information of one structural element) and a learning image that shows the one structural element. As a result of this machine learning, an identification model is created. The identification model is a model for identifying, on the basis of feature values of respective regions in an image that shows a structural formula of a compound, structural elements shown by the respective regions, among structural elements in the structural formula. The identification model will be described in detail in the following section.

The information processing apparatus has a function of detecting, from a document into which an image showing a structural formula of a compound is inserted, the image (subject image). The detected subject image is input to the identification model described above. Accordingly, structural elements in a structural formula of a compound (subject compound) shown by the subject image are identified.

Further, the information processing apparatus obtains element information about the identified structural elements in the subject compound. In the present embodiment, element information includes information indicating the type of each identified structural element and information indicating the location of the structural element.

In the present embodiment, information indicating the type of a structural element is information indicating the type of an atom or a bond between atoms corresponding to the structural element, and corresponds to "Bend C", "O", or "Double" in the case of the compound illustrated in FIG. 1.

Information indicating the location of a structural element is information indicating the location of the structural element in a coordinate space set for the subject image (for example, a two-dimensional coordinate space in which the lateral direction of the subject image is assumed to be an X direction and the longitudinal direction thereof is assumed to be a Y direction). In the present embodiment, a reference position (for example, the position of the top left vertex) of the subject image is assumed to be the origin, and as the location of a structural element, a representative position and the size (for example, the length in the X direction and that in the Y direction) of a rectangular region in which the structural element is enclosed are expressed in units of pixels.

Element information is obtained for each of the plurality of structural elements included in a structural formula of a subject compound. The obtained element information is stored in association with the subject compound. As illustrated in FIGS. 2A and 2B, for example, element information is stored so as to be linked with, for example, a document into which an image showing the structural formula of the subject compound is inserted.

In the present embodiment, of the element information, information indicating the types of structural elements is automatically obtained by the identification model identifying the structural elements in the structural formula. Of the element information, information indicating the location of a structural element is automatically obtained by analyzing an image (that is, a subject image) that includes a region showing the structural element.

The information processing apparatus repeatedly performs the series of processes described above (specifically, detection of an image from a document, identification of structural elements in the structural formula, and obtainment and storage of element information) for various subject compounds. Accordingly, as information about subject compounds, element information about structural elements in a structural formula of each of the subject compounds is accumulated. As a result, a database that contains element information for each subject compound is created (see FIGS. 2A and 2B).

The information processing apparatus includes a function of searching for a subject compound that is a target, that is, a subject compound corresponding to a search compound, by using element information stored in the database as a search key. For example, a user performing a search inputs image information indicating a structural formula of a search compound. The information processing apparatus obtains the image information as input information and searches for a subject compound that corresponds to the search compound, among subject compounds for which element information is stored, on the basis of the obtained input information and element information stored in the database.

As described above, with the information processing apparatus, it is possible to detect an image of a structural formula of a compound included in a document, such as a paper or a patent specification, and create a database that stores information (element information) about structural elements in the structural formula shown by the image. The use of the database can facilitate a search for a target compound. Accordingly, for example, it is possible to easily find a document into which an image showing a structural formula of a target compound is inserted.

Identification Model

The identification model used in the present embodiment (hereinafter referred to as an identification model MD will be described.

Figure 3:
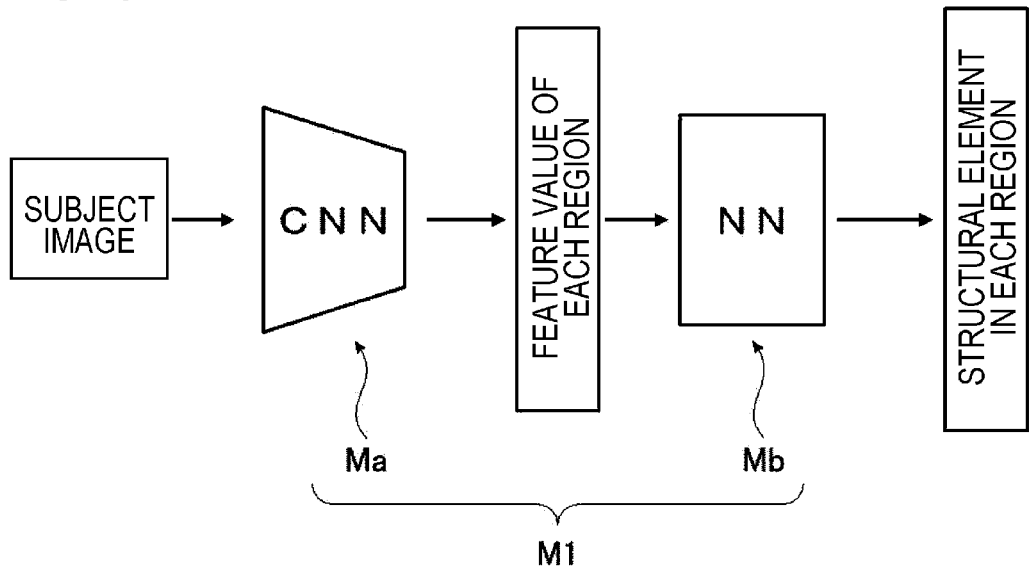
FIG. 3 is a schematic diagram of an identification model.

The identification model M1 is a model for identifying from an image (subject image) showing a structural formula of a subject compound, structural elements included in the structural formula. As illustrated in FIG. 3, the identification model M1 of the present embodiment is constituted by a feature value deriving model Ma and a structural element output model Mb.

The feature value deriving model Ma is a model that, in response to input of a subject image, derives feature values of respective regions in the subject image. In the present embodiment, the feature value deriving model Ma is, for example, formed as a convolutional neural network (CNN) having a convolution layer and a pooling layer as a middle layer. Examples of the CNN model include the 16-layer CNN (VGG16) from the Oxford Visual Geometry Group, the Inception model (GoogLeNet) from Google, the 152-layer CNN (Resnet) by Kaiming He, and the improved Inception model (Xception) by Chollet.

To derive feature values of respective regions in a subject image by using the feature value deriving model Ma, the regions in the subject image are specified. Specifically, structural elements included in a structural formula shown by the subject image are detected, and regions in which the detected structural elements are respectively enclosed are specified on a structural element by structural element basis. Such a function of specifying regions is included in the feature value deriving model Ma by machine learning described below.

The feature values of the image output from the feature value deriving model Ma are learning feature values in the convolutional neural network CNN and are feature values specified in the course of typical image recognition (pattern recognition). The feature values of the respective regions derived by the feature value deriving model Ma are input to the structural element output model Mb on a region by region basis.

The structural element output model Mb is a model that, in response to input of the feature values of the respective regions derived by the feature value deriving model Ma on a region by region basis, outputs structural elements (for example, the types of structural elements) corresponding to the feature values on a region by region basis. In the present embodiment, the structural element output model Mb is formed as, for example, a neural network (NN).

To output structural elements corresponding to the feature values of the respective regions in the subject image, the structural element output model Mb of the present embodiment specifies a plurality of candidates (candidate structural elements) for each region. To the plurality of candidates specified for each region, the softmax function is applied to calculate the output probabilities for the respective candidates. The output probability is a numerical value indicating the degree of likelihood (accuracy), that is, to what degree each of the plurality of candidates is likely to correspond to a structural element shown by the region. The sum of n (n is a natural number) output probabilities obtained as a result of application of the softmax function is equal to 1.0.

The structural element output model Mb outputs a candidate determined in accordance with the output probabilities, that is, for example a candidate having the highest output probability, among the plurality of candidates specified for each region as a structural element shown by the region. Accordingly, in the present embodiment, each of the structural elements in the structural formula shown by the subject image is determined from among a plurality of candidates specified on the basis of the feature value of a corresponding one of the regions in the subject image, on the basis of the output probabilities of the respective candidates.

The identification model M1 described above (in other words, each of the two models Ma and Mb described above) is created through machine learning using a plurality of learning data sets each of which is a set of a learning image showing one structural element in a structural formula of a compound and a label (ground truth label) of the structural element.

From the viewpoint of increasing the accuracy of learning, the more the number of learning data sets used in machine learning is, the better, and the number of learning data sets is preferably 50000 or more.

In the present embodiment, the machine learning is supervised learning, and as its technique, deep learning (that is, a multi-layer neural network) is used; however, the present embodiment is not limited to this. The type (algorithm) of the machine learning may be unsupervised learning, semi-supervised learning, reinforcement learning, or transduction.

The machine learning technique may be genetic programming, inductive logic programming, a support vector machine, clustering, a Bayesian network, an extreme learning machine (ELM), or decision tree learning.

Further, as the method for minimizing an objective function (loss function) in machine learning of the neural network, the gradient descent method may be used or the backpropagation algorithm may be used.

Figure 4:
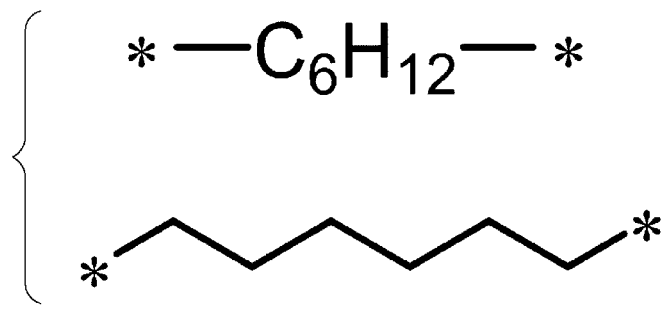
FIG. 4 is a diagram for explaining different depicting formats for a structural element.

In the machine learning of the present embodiment, a plurality of learning images that show structural elements having the same chemical structure and in different depicting formats may be used. For example, as illustrated in FIG. 4, when a certain structural element (a hexylene group is illustrated in FIG. 4) is depicted in equivalent depicting formats, a case may be assumed where machine learning is performed by using learning images provided in the respective depicting formats. Another case may be assumed where machine learning is performed by using a plurality of learning images among which, for example, the thickness, length, or orientation of a bond line between atoms differs but which show structural elements having the same chemical structure.

In the above-described cases, the identification model M1 (more specifically, the feature value deriving model Ma) that derives a common feature value from the plurality of learning images is created through machine learning. For example, to each of the learning images that show two hexylene groups in different depicting formats illustrated in FIG. 4, the same label "hexylene group" (ground truth label) is attached, and supervised learning is performed. Accordingly, the identification model M1 that can derive a common feature value from the learning images showing the two hexylene groups in different depicting formats and that can output the same structural element (hexylene group) from each of the images is created.

Configuration of Information Processing Apparatus of the Present Embodiment

Figure 5:
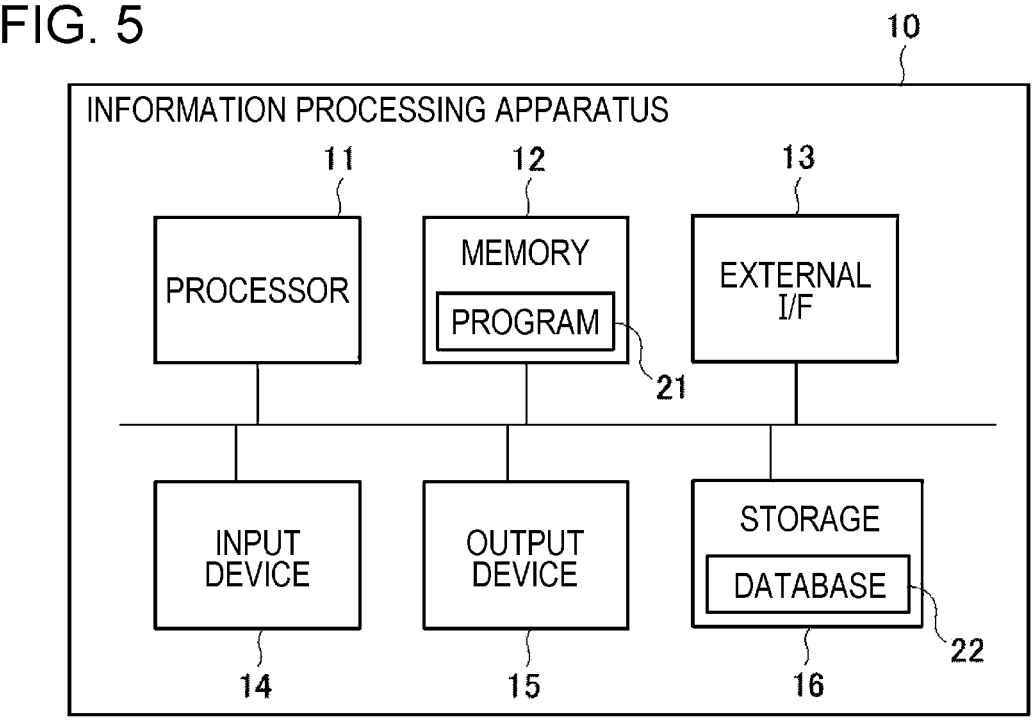
FIG. 5 is a diagram illustrating a configuration of an information processing apparatus according to one embodiment of the present invention.

Now, an example configuration of the information processing apparatus (hereinafter referred to as an information processing apparatus 10) illustrated in FIG. 5 will be described. In FIG. 5, an external interface is illustrated as "external I/F".

As illustrated in FIG. 5, the information processing apparatus 10 is a computer including a processor 11, a memory 12, an external interface 13, an input device 14, an output device 15, and a storage 16, which are electrically connected to each other.

Although the information processing apparatus 10 is constituted by a single computer in the present embodiment, the information processing apparatus 10 may be constituted by a plurality of computers.

The processor 11 is configured to execute a program 21 described below to perform processes for implementing the functions of the information processing apparatus 10 described above. The processor 11 is constituted by one or more CPUs (central processing units) and the program 21 described below.

The hardware processor that constitutes the processor 11 is not limited to a CPU and may be an FPGA (field-programmable gate array), a DSP (digital signal processor), an ASIC (application-specific integrated circuit), a GPU (graphics processing unit), an MPU (micro-processing unit), another type of IC (integrated circuit), or a combination thereof. The processor 11 may be a single IC (integrated circuit) chip, typically, an SoC (system on chip), that implements the overall functions of the information processing apparatus 10.

Note that the above-described hardware processor may be an electric circuit (circuitry) that is a combination of circuit elements, such as semiconductor elements.

The memory 12 is constituted by semiconductor memories, such as a ROM (read-only memory) and a RAM (random access memory), temporarily stores a program and data to thereby provide a work area of the processor 11, and temporarily stores various types of data generated as a result of processes performed by the processor 11.

In the memory 12, the program 21 for causing the computer to function as the information processing apparatus 10 of the present embodiment is stored. The program 21 includes programs p1 to p5 below.

p1: program for creating the identification model M1 through machine learning p2: program for detecting a subject image from a document into which the subject image is inserted p3: program for identifying structural elements in a structural formula shown by the subject image p4: program for storing element information about the identified structural elements p5: program for searching for a subject compound corresponding to a search compound, among subject compounds for which element information is stored Note that the program 21 may be obtained by reading from a computer-readable recording medium or may be obtained by receipt (download) via a network, such as the Internet or an intranet.

The external interface 13 is an interface for connecting with an external apparatus. The information processing apparatus 10 communicates with an external apparatus, such as a scanner or another computer on the Internet, via the external interface 13. Through such communication, the information processing apparatus 10 can obtain data for machine learning and obtain a document into which a subject image is inserted.

The input device 14 is constituted by, for example, a mouse and a keyboard and accepts an input operation by a user. The information processing apparatus 10 can obtain data for machine learning by, for example, the user using the input device 14 and drawing a structural element. To search for a subject compound corresponding to a search compound, the user inputs information about the search compound by operating the input device 14. Accordingly, the information processing apparatus 10 can obtain input information about the search compound.

The output device 15 is constituted by, for example, a display and a speaker and is a device that displays or outputs by sound reproduction, a subject compound (that is, a subject compound corresponding to a search compound) retrieved on the basis of the input information. The output device 15 can output element information stored for each subject compound in the database.

The storage 16 is constituted by, for example, a flash memory, an HDD (hard disc drive), an SSD (solid state drive), an FD (flexible disc), an MO disc (magneto-optical disc), a CD (compact disc), a DVD (digital versatile disc), an SD card (Secure Digital card), or a USB memory (Universal Serial Bus memory). In the storage 16, various types of data including data for machine learning are stored. In the storage 16, the identification model M1 and various models created through machine learning are also stored.

Further, in the storage 16, element information about structural elements in a structural formula of a subject compound identified by the identification model M1 is stored in association with the subject compound. As a result, a database 22 of element information illustrated in FIGS. 2A and 2B is created in the storage 16.

In the database 22, for each subject compound, element information about structural elements included in a structural formula of the subject compound, specifically, the type and location of each structural element, is accumulated.

The type of structural element stored in the database 22 is, as illustrated in FIG. 2B, the type of a structural element for which the output probability calculated by the identification model M1 is highest, and is stored together with the output probability (illustrated as "accuracy" in FIG. 2B).

The location of a structural element stored in the database 22 is a position expressed in the coordinate space in which the reference position of the subject image is assumed to be the origin, and is expressed by, for example, the representative position of a rectangular region in which the structural element is enclosed, the length in the X direction, and the length in the Y direction.

As illustrated in FIGS. 2A and 2B, element information about structural elements in a structural formula of a subject compound is stored so as to be linked with information about a document into which an image (subject image) showing the structural formula is inserted. Examples of information about a document include the title and so on of a paper when the document is a paper, the publication number and so on of an official gazette when the document is an official gazette, a page of the document into which the subject image is inserted, and the location and so on of the subject image in the page.

In the present embodiment, the storage 16 is a device incorporated into the information processing apparatus 10; however, the present embodiment is not limited to this. The storage 16 may be an external device connected to the information processing apparatus 10. The storage 16 may be an external computer (for example, a server computer for a cloud service) connected via a network such that communication is possible. In this case, the database 22 described above may be stored, in part or in whole, on the external computer that constitutes the storage 16.

The hardware configuration of the information processing apparatus 10 is not limited to the above-described configuration, and any structural device can be added, omitted, or replaced as appropriate in accordance with the specific embodiment.

Flow of Information Processing

Now, a flow of information processing using the information processing apparatus 10 will be described.

In the flow of information processing described below, the information processing method of the present invention is employed. That is, steps in the flow of information processing described below constitute the information processing method of the present invention.

Figure 6:
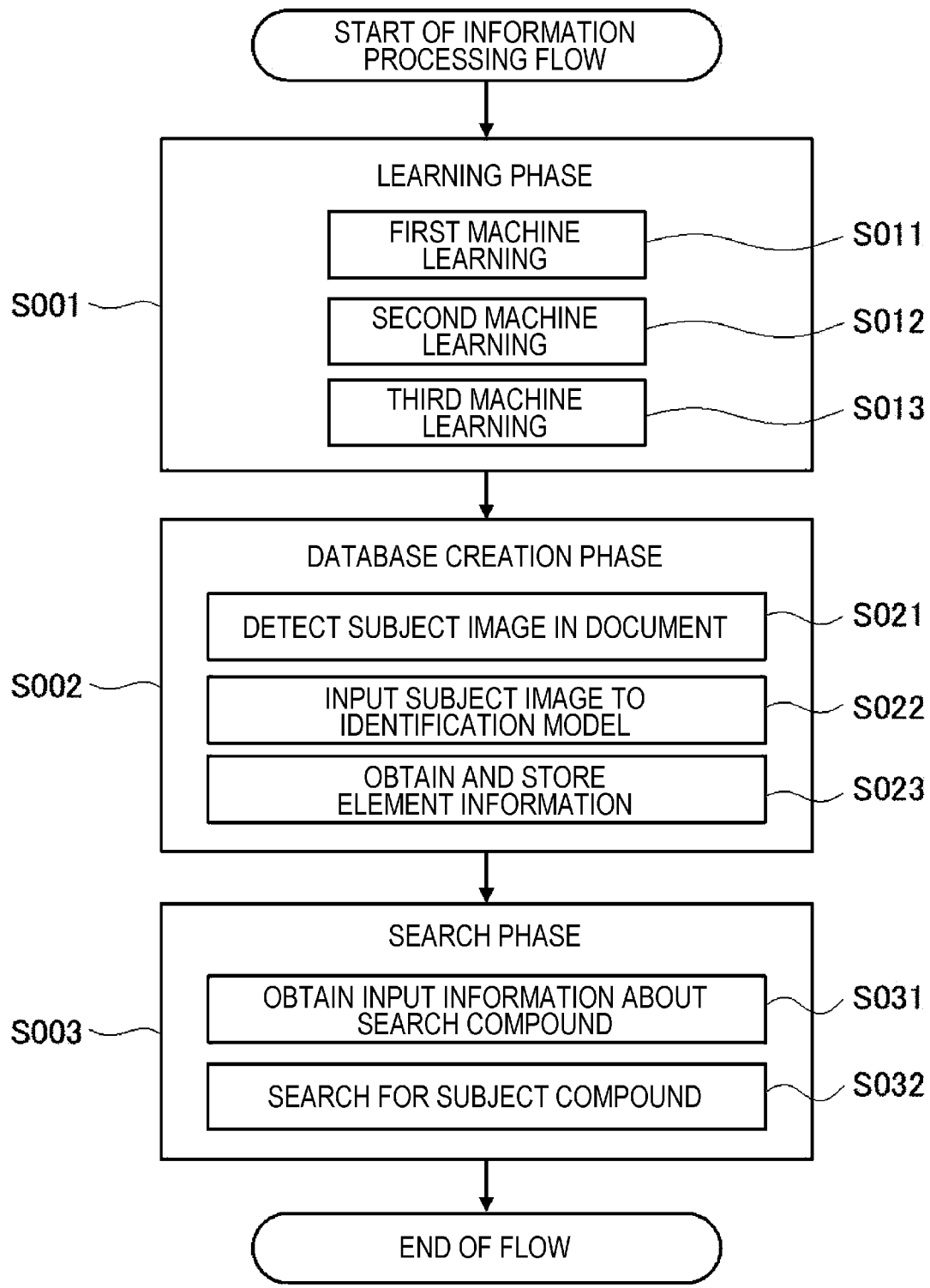
FIG. 6 is a diagram illustrating a flow of information processing using the information processing apparatus according to one embodiment of the present invention.

The flow of information processing of the present embodiment proceeds in the order of a learning phase S001, a database creation phase S002, and a search phase S003 as illustrated in FIG. 6. Each of the phases will be described below.

Learning Phase

The learning phase S001 is a phase in which machine learning is performed to create models necessary in the subsequent phases. In the learning phase S001, first machine learning S011, second machine learning S012, and third machine learning S013 are performed as illustrated in FIG. 6.

The first machine learning S011 is machine learning for creating the identification model M1 and is performed by using a learning image showing one structural element in a structural formula of a compound as described above. In the present embodiment, supervised learning is performed as the first machine learning S011. In the supervised learning, a learning image and a label (ground truth label) of one structural element shown by the learning image are used.

In the first machine learning S011, a plurality of learning images showing structural elements having the same chemical structure and in different depicting formats may be used as described above. Accordingly, the identification model M1 (specifically, the feature value deriving model Ma) that derives a common feature value from the plurality of learning images is created.

The second machine learning S012 is machine learning for creating a model (hereinafter referred to as an image detection model) that detects an image showing a structural formula of a compound from a document into which the image is inserted. The image detection model is a model for detecting an image of a structural formula from a document by using an object detection algorithm. As the object detection algorithm, R-CNN (Region-based CNN), Fast R-CNN, YOLO (You Only Look Once), and SSD (Single Shot Multibox Detector) are available. In the present embodiment, an image detection model using YOLO is created from the viewpoint of the detection speed.

Learning data (teaching data) used in the second machine learning S012 is created by applying an annotation tool to a learning image showing a structural formula of a compound. The annotation tool is a tool for adding to subject data, a ground truth label (tag) and related information including the coordinates of the subject as an annotation. When the annotation tool is activated, a document including a learning image is displayed, a region showing a structural formula of a compound is enclosed by a bounding box, and annotation is performed for the region, learning data is created.

As the annotation tool, for example, labelImg from tzutalin and VoTT from Microsoft are available.

When the second machine learning S012 is performed by using the above-described learning data, the image detection model, which is an object detection model in the YOLO format, is created.

The third machine learning S013 is machine learning for creating a model (hereinafter referred to as a search model) that searches for a subject compound corresponding to a search compound, among a plurality of subject compounds for which element information is stored in the database 22.

The search model of the present embodiment is a model that retrieves, as the search compound, a subject compound having a structural formula the same as or similar to that of the search compound, from among subject compounds for which element information is stored in the database 22.

It is assumed below that input information is information about structural elements included in a structural formula of a search compound and is, for example, image information showing the structural formula of the search compound. However, the input information may be other information as long as the other information includes content with which at least a part of the structural formula of the search compound can be specified (that is, the other information includes information that can be a key for searching the database 22 for the search compound). For example, the input information may be image information that shows some of the structural elements in the structural formula of the search compound. As the input information, information that corresponds to element information (for example, information indicating the type of a structural element in the structural formula and the location of the structural element in the structural formula) may be used. Further, the structural formula of the search compound may be drawn in part or in whole by using publicly available structural formula drawing software, such as ChemDraw (registered trademark) or RDKit, and the drawing data may be used as the input information.

The search model is constituted by a search compound specifying model and a degree-of-similarity evaluation model. The search compound specifying model is a model that specifies a structural formula of a search compound indicated by input information. In the present embodiment, when image information is input to the search compound specifying model as input information, information about structural elements in a structural formula indicated by the image information (for example, information indicating the type of each structural element and the location of the structural element in the structural formula) is output.

Note that as the search compound specifying model, the identification model M1 described above may be used, and as machine learning in this case, transfer learning may be performed.

The degree-of-similarity evaluation model evaluates the degree of similarity between a structural formula of a search compound specified by the search compound specifying model and a structural formula of a subject compound for which element information about structural elements is stored in the database 22. In the present embodiment, the degree of similarity is evaluated on the basis of element information about structural elements included in the structural formula of the search compound and element information about structural elements included in the structural formula of the subject compound.

Although the algorithm of the degree-of-similarity evaluation model is not limited to a specific one, a publicly available algorithm for evaluating, for example, the degree of similarity between images or the degree of calculation between pieces of text can be used. For example, an algorithm, in which element information about structural elements included in each structural formula is vectorized and the degree of similarity between vectors is calculated on the basis of an indicator, such as the Euclidean distance, can be used.

For a plurality of structural formulae of the same compound drawn in different depicting formats, it is preferable to increase the degree of similarity. This is because among structural formulae of the same compound depicted in different depicting formats, for example, the way of drawing of each functional group (for example, the orientation of a bond line) and the position of each atom differ. Taking into consideration such differences, the degree of similarity between structural formulae of the same compound depicted in different depicting formats needs to be increased. For example, for a plurality of structural formulae of the same compound depicted in different depicting formats and recorded to the database 22, the plurality of structural formulae need to be offered to machine learning with the same label (ground truth label) attached thereto, thereby creating the degree-of-similarity evaluation model.

The technique for evaluating the degree of similarity is not limited to that based on machine learning. For example, the degree of similarity may be evaluated on the basis of the result of comparing each structural element in a structural formula of a search compound and a corresponding structural element in a structural formula of a subject compound with each other in accordance with a comparison rule defined in advance. The degree of similarity may be evaluated by grouping subject compounds, for each of which element information about structural elements is stored in the database 22, into clusters on the basis of the element information and by specifying a cluster to which the search compound belongs.

The third machine learning S013 is performed by using element information about structural elements in a structural formula, which is stored in the database 22 for each subject compound, and learning information about a structural formula of a compound. The learning information is, for example, information about a compound selected for the third machine learning S013 and indicates, for example, the types and locations of structural elements in a structural formula of the compound.

When the third machine learning is performed, the search model described above is created.

Database Creation Phase

The database creation phase S002 is a phase in which for a structural formula of a subject compound shown by an image (subject image) included in a document, element information about structural elements in the structural formula is stored to create the database 22.

In the database creation phase S002, first, the processor 11 of the information processing apparatus 10 applies the image detection model described above to a document that includes a subject image and detects the subject image in the document (S021). That is, in step S021, the processor 11 uses the object detection algorithm (specifically, YOLO) and detects the subject image from the document.

At this time, when a plurality of subject images are included in one document, the processor 11 detects the plurality of subject images (images of parts outlined by dashed lines in FIG. 7) from the document as illustrated in FIG. 7.

Next, the processor 11 identifies, on the basis of feature values of respective regions in the subject image, structural elements in a structural formula of the subject compound by using the identification model M1 (S022).

Specifically, the processor 11 inputs the subject image detected in step S021 to the identification model M1. The feature value deriving model Ma, which is the preceding stage in the identification model M1, outputs feature values of respective regions in the subject image. The structural element output model Mb, which is the succeeding stage therein, outputs, on the basis of input of the feature values of the respective regions, structural elements (specifically, the types of structural elements). At this time, on the basis of the feature value of each region, a plurality of candidates for a structural element corresponding to the region are specified, and the output probabilities are calculated for the respective candidates.

The structural element output model Mb outputs a candidate having the highest output probability as a structural element shown by the region as described above. When structural elements shown by the respective regions in the subject image are output on a region by region basis, a structural formula shown by the subject image (that is, a structural formula of the subject compound) can be identified on a structural element by structural element basis.

When a plurality of subject images are detected in step S021, the processor 11 inputs the plurality of detected subject images to the identification model M1 on a subject image by subject image basis. Accordingly, for each subject image among the plurality of subject images, structural elements in a structural formula of a subject compound shown by the subject image are identified.

Next, the processor 11 obtains element information about the identified structural elements in the structural formula of the subject compound and stores the obtained element information (S023). At this time, the processor 11 stores the element information about the structural elements in association with the subject compound that includes the structural elements in the structural formula. In the present embodiment, the element information about the structural elements is stored so as to be linked with, for example, information about the document into which the image (subject image) of the structural formula constituted by the structural elements is inserted (see FIGS. 2A and 2B).

Step S023 is repeated each time structural elements in a structural formula of a new subject compound are identified. As a result, element information about structural elements in a structural formula of each subject compound is accumulated, and the database 22 of element information is created. A subject compound for which element information is stored in the database 22 is searchable in the subsequent search phase S003 by using the element information as a key.

Search Phase

The search phase S003 is a phase in which a search for a subject compound corresponding to a search compound among subject compounds for which element information is stored in the database 22 is performed. The "search compound" is a search target. Information about a structural formula of the search compound is obtained in part or in whole as input information at the time of a search.

In the search phase S003, first, the processor 11 of the information processing apparatus 10 obtains input information about a search compound (S031). In step S031, the processor 11 obtains information about structural elements included in a structural formula of the search compound as input information. Examples of such information include image information showing the structural formula of the search compound.

After obtaining the input information, the processor 11 searches for a subject compound corresponding to the search compound among subject compounds for which element information is stored in the database 22, by using the search model described above (S032). Specifically, the processor 11 calculates the degree of similarity between the search compound and a subject compound by using the search model on the basis of the obtained input information and element information stored in the database 22 in association with the subject compound. In the present embodiment, the processor 11 calculates the degree of similarity of the structural formulae between the search compound indicated by the input information and a subject compound for which element information is stored in the database 22.

Subsequently, the processor 11 retrieves (selects), as the search compound, a subject compound for which the calculated degree of similarity satisfies a search condition, from among subject compounds for which element information is stored in the database 22. The search condition is a condition determined in advance for selecting a subject compound corresponding to the search compound on the basis of the result of calculation of the degree of similarity. In the present embodiment, a predetermined number of subject compounds are retrieved as the search compound in descending order of degree of similarity. However, the present embodiment is not limited to this, and only a subject compound having the highest degree of similarity may be retrieved as the search compound. A subject compound having a degree of similarity greater than or equal to a reference value may be retrieved as the search compound.

The processor 11 outputs information about the retrieved subject compounds via the output device 15 and, for example, displays the search results on a screen as illustrated in FIG. 8. Examples of information about a retrieved subject compound include, for example, a document and a page of the document into which an image showing a structural formula of the subject compound is inserted. As illustrated in FIG. 8, it is preferable to output the degree of similarity between each retrieved subject compound and the search compound, together with the search results of subject compounds.

A case is possible where, as input information about a search compound, information indicating some of the structural elements included in a structural formula of the search compound (hereinafter referred to as "partial structure" for the sake of convenience) is obtained. In such as case, a subject compound that includes the partial structure is retrieved as the search compound. Specifically, for each subject compound for which element information is stored in the database 22, the degree of similarity between a partial structure included in a structural formula of the subject compound and the partial structure indicated by the input information is calculated. Then, a predetermined number of subject compounds are retrieved as the search compound in descending order of degree of similarity.

Effectiveness of the Present Embodiment

The information processing apparatus 10 of the present embodiment can identify, on the basis of feature values of respective regions in an image (subject image) showing a structural formula of a subject compound, structural elements in the structural formula by using the identification model M1 created in the first machine learning S011. The information processing apparatus 10 of the present embodiment stores element information about the identified structural elements in association with the subject compound to create the database 22. The element information stored in the database 22 can be used as a search key in a search for the subject compound performed later on.

The above-described effects will be described in detail below. In the related art, a rule is established on correspondences between regions in an image that shows a structural formula of a compound and structural elements, in the structural formula, present in the respective regions. Then, the structural elements in the structural formula are identified in accordance with the rule. However, when the way of drawing of the structural formula is changed, it might not be possible to identify the structural elements in the structural formula unless an identification rule adaptable to the way of drawing is established. In this case, for the reason that, for example, the results of identification of the structural elements are not available, it is difficult to search for the structural formula that includes the structural elements.

In contrast, in the present embodiment, structural elements in a structural formula can be identified from feature values of respective regions in a subject image by using the identification model M1, which is the outcome of machine learning. That is, in the present embodiment, even when the way of drawing of a structural formula is changed, feature values of respective regions in an image showing the structural formula are specified, and when the feature values can be specified, structural elements can be determined (identified) from the feature values. Element information about the identified structural elements is stored in association with the subject compound to create a database. Therefore, a search for the subject compound that is a target can be performed later on by using the element information as a search key.

As described above, according to the present embodiment, even when the way of drawing of a structural formula of a subject compound is changed, structural elements in the structural formula can be satisfactorily identified. A search for the subject compound that is a target can be appropriately performed by using element information about the identified structural elements as a search key.

Other Embodiments

Although the information processing apparatus, the information processing method, and the program of the present invention have been described above with specific examples, the above-described embodiment is only an example and other embodiments may be possible.

For example, the computer that constitutes the information processing apparatus may be a server used in, for example, an ASP (Application Service Provider), SaaS (Software as a Service), a PaaS (Platform as a Service), or an IaaS (Infrastructure as a Service). In this case, a user using a service, such a service of an ASP described above, operates a terminal not illustrated and transmits input information about a search compound to the server. When receiving the input information, the server searches for a subject compound corresponding to the search compound, among subject compounds for which element information is stored, on the basis of the input information. The server outputs (transmits) information about the search results (that is, subject compounds corresponding to the search compound) to the user's terminal. On the user's side, the information (that is, the search results) transmitted from the server is displayed or output by sound reproduction.

In the above-described embodiment, individual atoms and each individual bond between atoms included in a structural formula are assumed to be structural elements; however, the present embodiment is not limited to this. For example, a functional group (atomic group) including a plurality of atoms may be assumed to be a structural element. In this case, of element information about a structural element, information indicating the type of the structural element needs to be information indicating the chemical formula of a functional group corresponding to the structural element.

A plurality of functional groups adjacent to each other in a structural formula may be assumed to be a structural element, or each of the fragments obtained by dividing a structural formula in accordance with a desired rule may be assumed to be a structural element.

Of element information, information indicating the type of structural element may be information formed of a part of a molecular fingerprint about a structural formula of the subject compound. The molecular fingerprint is a binary multidimensional vector indicating, for each type of structural element, the presence or absence of the structural element in the structural formula. For example, for a functional group illustrated on the left side of FIG. 9, a molecular fingerprint illustrated on the right side of FIG. 9 is set.

In the above-described embodiment, machine learning (first to third machine learning) for creating various models is performed by the information processing apparatus 10; however, the present embodiment is not limited to this. The machine learning may be performed, in part or in whole, by an apparatus (computer) other than the information processing apparatus 10. In this case, the information processing apparatus 10 obtains a model created through machine learning performed by the other apparatus.

For example, when the first machine learning is performed by the other apparatus, the information processing apparatus 10 obtains the identification model M1 from the other apparatus and identifies structural elements in a structural formula shown by a subject image by using the obtained identification model M1.

REFERENCE SIGNS LIST 10 information processing apparatus
11 processor
12 memory
13 external interface
14 input device
15 output device 16 storage
21 program
22 database
M1 identification model
Ma feature value deriving model
Mb structural element output model

What is claimed is:

1. An information processing apparatus comprising a processor,
the processor being configured to
identify, on the basis of feature values of respective regions in a subject image showing a structural formula of a subject compound, structural elements shown by the respective regions among structural elements in the structural formula of the subject compound, by using an identification model, and
store element information about the identified structural elements in the structural formula of each subject compound in association with the subject compound,
the identification model being created through machine learning using a plurality of learning images, each of the plurality of learning images showing one structural element in a structural formula of a compound.

2. The information processing apparatus according to claim 1, wherein when the plurality of learning images, each showing the structural element having the same chemical structure but depicted in different formats from each other, are used in the machine learning, the identification model that derives a common feature value from the plurality of learning images is created through the machine learning.

3. The information processing apparatus according to claim 2, wherein
the processor is configured to
obtain input information about a search compound, and
search for the subject compound corresponding to the search compound, among the subject compounds for each of which the element information is stored, on the basis of the input information and the element information associated with each subject compound.

4. The information processing apparatus according to claim 3, wherein
the processor is configured to
calculate a degree of similarity between the search compound and each subject compound on the basis of the input information and the element information stored in association with the subject compound, and
retrieve, as the search compound, the subject compound for which the degree of similarity satisfies a search condition, from among the subject compounds for each of which the element information is stored.

5. The information processing apparatus according to claim 2, wherein
the processor is configured to
detect the subject image from a document that includes the subject image, and
identify the structural elements shown by the respective regions in the subject image by inputting the detected subject image in the identification model.

6. The information processing apparatus according to claim 5, wherein the processor is configured to detect the subject image from the document by using an object detection algorithm.

7. The information processing apparatus according to claim 2, wherein the element information includes information indicating a type of each structural element among the identified structural elements in the structural formula of the subject compound.

8. The information processing apparatus according to claim 1, wherein
the processor is configured to
obtain input information about a search compound, and
search for a subject compound corresponding to the search compound, among the subject compounds for each of which the element information is stored, on the basis of the input information and the element information associated with each subject compound.

9. The information processing apparatus according to claim 8, wherein
the processor is configured to
calculate a degree of similarity between the search compound and each subject compound on the basis of the input information and the element information stored in association with the subject compound, and
retrieve, as the search compound, a subject compound for which the degree of similarity satisfies a search condition, from among the subject compounds for each of which the element information is stored.

10. The information processing apparatus according to claim 9, wherein the processor is configured to obtain the input information that is information about the structural element included in a structural formula of the search compound.

11. The information processing apparatus according to claim 8, wherein the processor is configured to obtain the input information that is information about a structural element included in a structural formula of the search compound.

12. The information processing apparatus according to claim 1, wherein
the processor is configured to
detect the subject image from a document that includes the subject image, and
identify the structural elements shown by the respective regions in the subject image by inputting the detected subject image in the identification model.

13. The information processing apparatus according to claim 12, wherein the processor is configured to detect the subject image from the document by using an object detection algorithm.

14. The information processing apparatus according to claim 1, wherein the element information includes information indicating a type of each structural element among the identified structural elements in the structural formula of the subject compound.

15. The information processing apparatus according to claim 14, wherein the information indicating the type of each structural element among the structural elements is information indicating a type of an atom or a bond between atoms corresponding to the structural element.

16. The information processing apparatus according to claim 14, wherein the information indicating the type of each structural element among the structural elements is information indicating a chemical formula of a functional group corresponding to the structural element.

17. The information processing apparatus according to claim 14, wherein the information indicating the type of each structural element among the structural elements is information formed of a part of a molecular fingerprint indicating, for each type of structural element, presence or absence of the structural element in the structural formula of the subject compound.

18. The information processing apparatus according to claim 1, wherein the element information further includes information indicating a location of each structural element among the identified structural elements in the structural formula of the subject compound, in a coordinate space set for the subject image.

19. An information processing method in which a processor is configured to perform
- a step of identifying, on the basis of feature values of respective regions in a subject image showing a structural formula of a subject compound among subject compounds, structural elements shown by the respective regions among structural elements included in the structural formula of the subject compound, by using an identification model, and
- a step of storing element information about the identified structural elements in the structural formula of each subject compound in association with the subject compound,
- the identification model being created through machine learning using a learning image showing one structural element in a structural formula of a compound.

20. A non-transitory computer readable medium storing a program for causing a processor to perform the steps in the information processing method according to claim 19.

* * * * *